United States Patent [19]

Spotorno et al.

[11] Patent Number: 5,080,678
[45] Date of Patent: Jan. 14, 1992

[54] ARTIFICIAL ACETABULUM

[75] Inventors: Lorenzo Spotorno, Ligure, Italy; Rudolf Koch, Berlingen; Roland Willi, Stadel, both of Switzerland

[73] Assignee: Sulzer Brothers Limited, Winterthur, Switzerland

[21] Appl. No.: 662,171

[22] Filed: Feb. 28, 1991

[30] Foreign Application Priority Data

Mar. 1, 1990 [CH] Switzerland ............ 00643/90

[51] Int. Cl.[5] ............................................. A61F 2/32
[52] U.S. Cl. ............................................. 623/22; 623/18
[58] Field of Search ........................ 623/16, 18, 22, 23

[56] References Cited

U.S. PATENT DOCUMENTS

| | | | |
|---|---|---|---|
| 4,718,914 | 1/1988 | Frey et al. | 623/22 X |
| 4,770,661 | 9/1988 | Oh | 623/22 X |
| 4,813,961 | 3/1989 | Sostegni | 623/22 |
| 4,969,910 | 11/1990 | Frey et al. | 623/22 |
| 5,021,063 | 6/1991 | Täger | 623/22 X |

FOREIGN PATENT DOCUMENTS

| | | |
|---|---|---|
| 0066092 | 12/1982 | European Pat. Off. . |
| 0253941 | 1/1988 | European Pat. Off. ............ 623/22 |
| 0190446 | 3/1989 | European Pat. Off. ............ 623/22 |
| 0329019 | 8/1989 | European Pat. Off. ............ 623/18 |
| 0077518 | 9/1977 | Luxembourg . |
| 2069338 | 8/1981 | United Kingdom ............ 623/22 |

Primary Examiner—Ronald Frinks
Attorney, Agent, or Firm—Kenyon & Kenyon

[57] ABSTRACT

An artificial acetabulum is made with a metal inner shell, a thin outer shell which defines a cavity with the inner shell and an elastic force-transmitting member between the two shells to damp forces imposed on the shells. In addition, a metal gauze layer is disposed about the outer shell for the ingrowth of osseous tissue. The inner and outer shells are connected at the edges so as to impermeable to air so that no particles from the cavity between the shells can reach the surrounding environment. A beading is also provided on the outer shell and/or gauze so as to snap into an appropriate undercut in the osseous tissue during primary implantation.

15 Claims, 3 Drawing Sheets

5,080,678

ARTIFICIAL ACETABULUM

This invention relates to an artificial acetabulum. More particularly, this invention relates to an artificial acetabulum which is made of metal and which is to be used without the need for bone cement.

As is known, various types of acetabula have been used for replacing a hip joint. In some cases, the acetabulum has been constructed so as to elastically deform to a limited extent in order to take up shocks between a spherical head of a joint prosthesis and the acetabulum caused by walking and running. For example U.K. Patent Application 2,069,338 describes a joint socket intended for the spherical head of a hip joint femur prosthesis which comprises a cylindrical cup of metal, an insert of plastic material within the cup and a buffer of elastically yielding material between the plastic insert and the metal cup. European Patent Application 0066092 and 0253941 described similar acetabula constructions.

Luxembough Patent 77518 describes an acetabulum which employs a spring on the femur prosthesis to permit springing of a hemispherical head of the prosthesis.

European Patent Application 0 190 446 describes another type of artificial acetabulum wherein a metal hollow body having an approximately constant wall thickness is filled with an elastic material having an invariable volume.

It has also been known from European Patent Application 0329019 to provide a two-part acetabulum having a pair of shells spaced apart to define a cavity into which bone may grow through perforations in the outer shell.

However, the above described acetabula generally have a limited damping effect between the inner and outer shells since small relative movements are possible between the inner and outer shells. Further, when introducing the acetabulae into osseous tissue, the use of force results in stress peaks which are caused by the relatively rigid geometry of the outer shell. Thus, local overstressing from the fused osseous tissue and detachment resulting therefrom cannot be excluded with an inherently stable outer shell. In the same way, changes in the original bone structure which result in a local change in elasticity produce a weakening of the bond between the outer shell and the osseous tissue.

Accordingly, it is an object of the invention to provide, within certain limits, the tissue-contacting surface of the outer shell of an acetabulum with a similar local rigidity with respect to compressive forces as the fusing osseous tissue.

It is another object of the invention to provide an artificial acetabulum which has elastic properties and which can be readily implanted without the need for the bone cement.

It is another object of the invention to provide an artificial acetabulum which can be locally deformed during implantation and which provides for elasticity in a hip joint.

Briefly, the invention provides an artificial acetabulum comprising an inner shell defining a cavity and a thin flexible outer shell which is disposed in spaced relation to the inner shell in order to define a cavity therebetween and which is secured to the inner shell at an edge thereof in air sealed relation. In addition, the acetabulum has at least one elastic force-transmitting member in the cavity in contact with each shell as well as a layer of thin flexible metal gauze on the outer shell for contacting osseous tissue.

The two shells are connected securely to one another at the respective edges so as to be impermeable to air. This has the advantages that, after insertion of the acetabulum, neither abrasion nor other particles in the cavity between the shells can reach the surrounding tissue.

In addition, at least one of the metal gauze and the outer shell has a circumferential beading adjacent the edge of the outer shell for supporting a primary attachment to undercut osseous tissue. Thus, when the acetabulum is being implanted, the beading serves to hold the acetabulum in place until there has been sufficient bone growth into the metal gauze to provide for a permanent fixation of the acetabulum in the bone.

The outer shell is constructed with a relatively thin wall so as to be deformable inwardly towards the inner shell, within prescribed limits, under forces acting from the outside inwardly.

The construction of the acetabulum is such that an equilibrium of forces, without stress peaks, occurs between the out shell and the fusing osseous tissue when stress reversal occurs. The outer shell also adapts to longer-term changes in the position of the surrounding osseous tissue by plastic deformation.

These and other objects and advantages of the invention will become more apparent from the following detailed description taken in conjunction with the accompanying drawings wherein.

Figure 1:
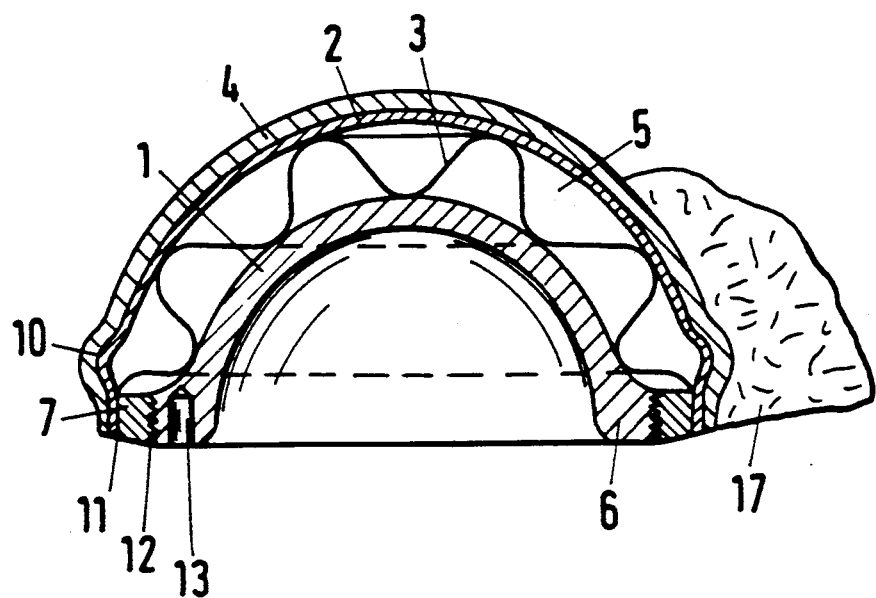
FIG. 1 illustrates a cross sectional view of an artificial acetabulum constructed in accordance with the invention.

Referring to FIG. 1, the acetabulum has a rigid inner shell 1 of metal, a thin flexible outer shell 2 disposed in spaced relation to the inner shell 1 in order to define a cavity 5 therebetween, an elastic force-transmitting member 3 disposed in the cavity 5 and in contact with each shell 1, 2 at a spaced apart points and a layer of thin flexible metal gauze 4 on the outer shell 2 for contacting osseous tissue 17.

Figure 4:
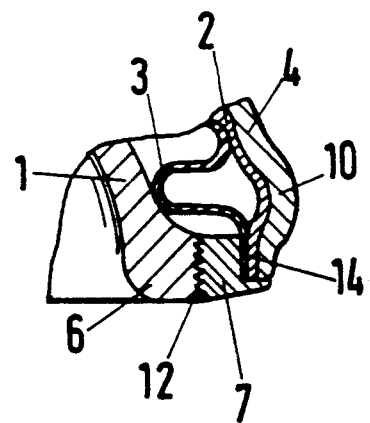
FIG. 4 illustrates a detailed view of a manner of connection of the inner and outer shells of an acetabulum in accordance with the invention.

Referring to FIGS. 1 and 4, the outer shell 2 is secured to the inner shell 1 at an edge thereof in air sealed relation. To this end, a thrust ring 7 is fixed to and within the edge of the outer shell 2 by means of a weld 14. As such, the thrust ring 7, outer shell 2, elastic member 3, and gauze 4 constitutes an assembly unit. In addition, the inner shell 1 is provided with a flange-like collar 6 at the edge for securement to the thrust ring 7 as by a weld 12.

Referring to FIG. 1, the collar 6 may be provided with an external thread while the thrust ring 7 is provided with an internal thread. In this way, the inner shell 1 may be screwed into the thrust ring 7 during assembly in order to prestress the elastic member 3 by compressing the member 3 between the two shells 1, 2.

As indicated in FIG. 1, the elastic member 3 is corrugated to contact the outer shell 2 at spaced apart points. Thus, the intermediate portions of the thin outer shell 2 are able to deform inwardly of the corrugations of the elastic member 3 during implantation in osseous tissue. The elastic member 3 may be made from a stamped metal sheet.

Further, the inner shell 1 may have a thickness of more than two millimeters so as to be rigid and non-deformable.

As shown in FIG. 1, both the outer shell 2 and the metal gauze 10 have a circumferential beading 10 adjacent the edge of the outer shell 2 for supporting a primary attachment to an undercut in the osseous tissue 17.

As also indicated in FIG. 1, the inner shell 1 may be provided with one or more blind bores 13 for receiving a suitable tool for screwing the inner shell 1 into the thrust ring 7. The correct stressing of the elastic transfer member 3 between the shells 1, 2 is determined during this screwing in operation at various references points on the outer shell 2 by measuring the rigidity in the direction of the shell center.

During the preassembly of the two shells 1, 2, the inner shell 1 is screwed into the thrust ring 7 and, after a prescribed initial stress in the elastic member 3 has been reached, the inner shell 1 is connected to the thrust ring 7 by the weld 12 along the mutual thread.

The circumferential beading 10 which is directed radially outwardly is shaped so as to be inwardly elastic.

Once the acetabulum has been implanted, osseous tissue may grow into the gauze 4 in order to provide a more permanent anchorage.

Figure 2:
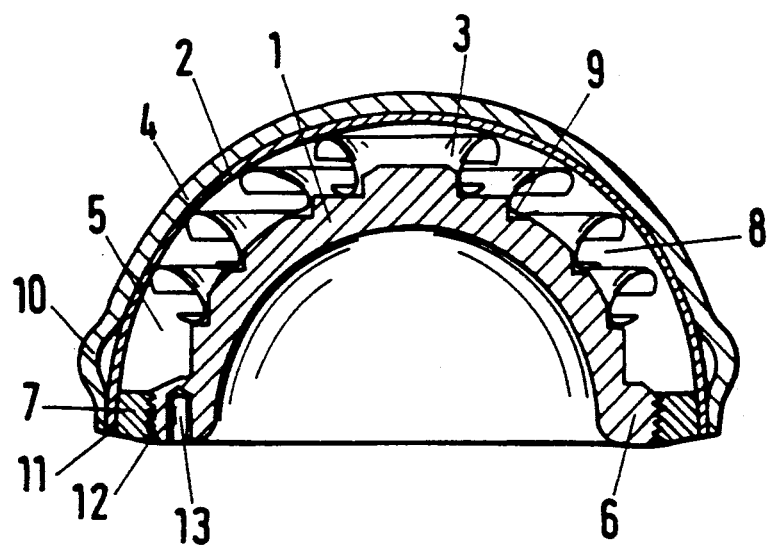
FIG. 2 illustrates a cross sectional view of a modified acetabulum in accordance with the invention employing a plurality of elastic members between the inner and outer shells.

Referring to FIG. 2, wherein like reference characters indicate like parts as above, the acetabulum, may be constructed with a plurality of elastic members 3. As indicated, the elastic members 3 are disposed concentrically within the cavity 5 while the inner shell 1 has centering steps 9 for the individual members 3. As indicated, each member is similar to a torus and has a C-shaped cross-section while being prestressed between the shells 1, 2. Each transfer member 3 may be formed of the hollow metal O-ring which is provided with a circumferential slit 8. The spring action of such an O-ring changes to a very much harder spring as soon as the slit 8 is compressed to zero. Non-linear spring systems of this type have the advantage that with extraordinary loads, the spring elongations are not too long and that the inherent stability of the entire acetabulum is maintained to some extent.

Figure 3:
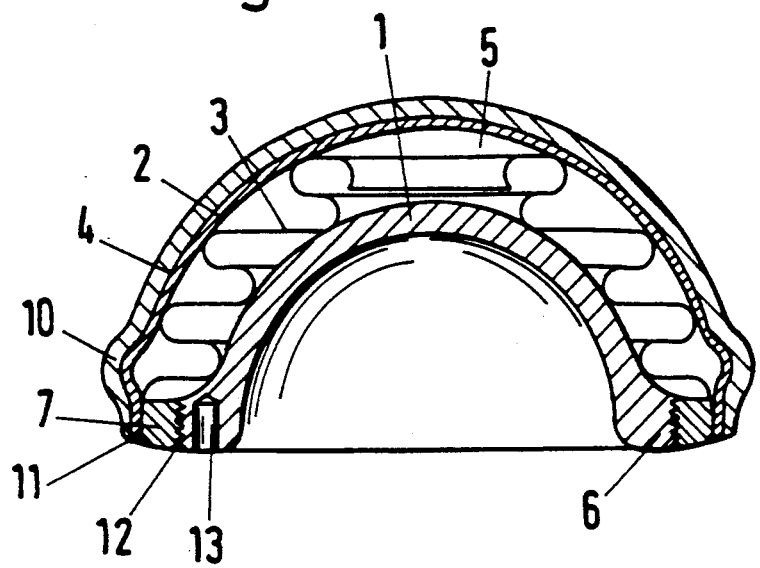
FIG. 3 illustrates a cross sectional view of a further modified acetabulum constructed in accordance with the invention.

Referring to FIG. 3, wherein like reference characters indicate like parts as above, the elastic member 3 may be corrugated in a different manner from that as illustrated in FIG. 1. For example, the corrugations are directed in substantially horizontal planes.

Referring to FIGS. 1 and 4, wherein like reference characters indicate like parts as above, the thrust ring 7 may be provided with a shouldered outer portion 11 so as to receive the outer shell 2, elastic member 3 and gauze 10 in a recessed manner. A suitable weld 14 may be used to secure the elements together at this point.

Figure 5:
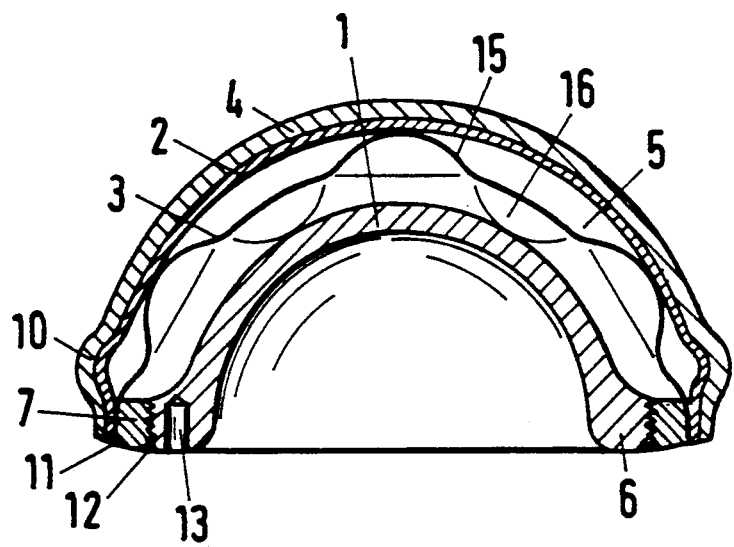
FIG. 5 illustrates a further modified acetabulum in accordance with the invention.
Figure 6:
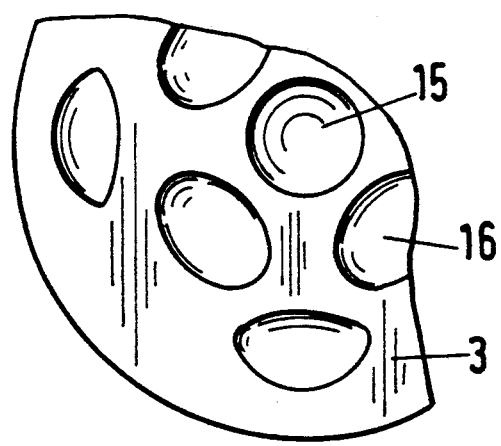
FIG. 6 illustrates a detailed view of the elastic member employed between the shells of the acetabulum of FIG. 5.

Referring to FIGS. 5 and 6, wherein like reference characters indicate like parts as above, the elastic force-transmitting member 3 may be in the form of a spherical shell having protuberances 15, 16 projecting from opposite sides so as to achieve a non-linear spring action. In this case, the protuberances 15, 16 are collapsible with the protuberances 15 transmitting member 3 may be in the form of a spherical shell having protuberances 15, 16 projecting from opposite sides so as to achieve a non-linear spring action. In this case, the protuberances 15, 16 are collapsible with the protuberances 15 abutting the outer shell 2 and the protuberances 16 abutting the inner shell 1.

The inner shell 1 provides sufficient rigidity to provide a reference point for the elastic member(s) 3 of the acetabulum as well as for the spherical end of an artificial hip joint. To this end, the wall thickness of the shell 1 is more than 2 millimeters.

The invention thus provides an artificial acetabulum of elastic construction which is able to absorb or damp stresses which are imposed upon the acetabulum during walking or running of a person in which the acetabulum is implanted. In addition, the acetabulum is constructed so as to be readily implanted in osseous tissue. In this respect, due to the elastic resilience of the outer shell, a state of equilibrium which does not appreciably permit local stress peaks, is produced when the hip joint is stressed towards the fusing osseous tissue.

What is claimed is:

1. An artificial acetabulum comprising:
   an inner shell defining a cavity;
   a thin flexible outer shell disposed in spaced relation to said inner shell to define a cavity therebetween and being secured to said inner shell at an edge thereof in air sealed relation;
   at least one elastic force-transmitting member in said cavity and in contact with each said shell; and
   a layer of thin flexible metal gauze on said outer shell for contacting osseous tissue.

2. An artificial acetabulum as set forth in claim 1 wherein at least one of said metal gauze and said outer shell has a circumferential beading adjacent said edge of said outer shell for supporting a primary attachment to undercut osseous tissue.

3. An artificial acetabulum as set forth in claim 1 wherein said inner shell is rigid and non-deformable.

4. An artificial acetabulum as set forth in claim 1 wherein said inner shell has a thickness of more than 2 millimeters.

5. An artificial acetabulum as set forth in claim 1 wherein said elastic member is corrugated.

6. An artificial acetabulum as set forth in claim 1 wherein said elastic member is a stamped metal sheet.

7. An artificial acetabulum as set forth in claim 1 which comprises a plurality of said elastic members disposed concentrically within said cavity.

8. An artificial acetabulum as set forth in claim 7 wherein each elastic member has a C-shaped cross-section.

9. An artificial acetabulum as set forth in claim 1 wherein said elastic member is a non-linear spring.

10. An artificial acetabulum as set forth in claim 1 which further comprises a thrust ring fixedly secured to and within said edge of said outer shell and threadably secured to said inner shell to permit pre-stressing of said elastic member between said shells.

11. An artificial acetabulum as set forth in claim 1 which further comprises a thrust ring fixedly secured to and within said edge of said outer shell and fixedly secured to said inner shell with said elastic member pre-stressed between said shells.

12. An artificial acetabulum comprising:

a rigid inner shell;

a thin flexible outer shell disposed in spaced relation to said inner shell to define a cavity therebetween and being secured to said inner shell at an edge thereof, said outer shell being deformable inwardly towards said inner shell;

at least one elastic force-transmitting member disposed in pre-stressed relation between said shells and in said cavity to contact spaced apart portions of said outer shell and to transfer forces therebetween; and a layer of deformable metal gauze on said outer shell for contact osseous tissue.

13. An artificial acetabulum as set forth in claim 12 wherein at least one of said metal gauze and said outer shell has a circumferential beading adjacent said edge of said outer shell for supporting a primary attachment to undercut osseous tissue.

14. An artificial acetabulum as set forth in claim 12 which comprises a plurality of said elastic members disposed concentrically within said cavity.

15. An artificial acetabulum as set forth in claim 12 which further comprises a thrust ring fixedly secured to and within said edge of said outer shell and secured to said inner shell.

* * * * *